United States Patent [19]

Assaker

[11] Patent Number: 5,620,444
[45] Date of Patent: Apr. 15, 1997

[54] CLAMP FOR STABILIZING A CERVICAL SPINE SEGMENT

[75] Inventor: Richard Assaker, Kain, Belgium

[73] Assignee: Sofamor S.N.C., Rang-du-Fliers, France

[21] Appl. No.: 433,364

[22] PCT Filed: Sep. 1, 1994

[86] PCT No.: PCT/EP94/02906

§ 371 Date: Oct. 3, 1995

§ 102(e) Date: Oct. 3, 1995

[87] PCT Pub. No.: WO95/06440

PCT Pub. Date: Mar. 9, 1995

[30] Foreign Application Priority Data

Sep. 3, 1993 [FR] France ..................... 93 10528

[51] Int. Cl.⁶ ..................................... A61B 17/70
[52] U.S. Cl. ............................... 606/61; 606/73
[58] Field of Search .................. 606/61, 53, 60, 606/72, 73, 74

[56] References Cited

U.S. PATENT DOCUMENTS

4,041,939  8/1977  Hall .
4,257,409  3/1981  Bacal et al. .

Primary Examiner—Guy V. Tucker
Assistant Examiner—David O. Reip
Attorney, Agent, or Firm—Woodard, Emhardt, Naughton, Moriarty & McNett

[57] ABSTRACT

The clamp (1) comprises a pair of hooks (2, 3) adapted to bear on at least two cervical vertebrae (for example C1, C2) and each having a tubular portion (6, 7). The diameters of the latter are such as to permit the fitting and the sliding of one portion in the other and consequently the adjustment of the relative position of the two hooks. They are fixed in this position by a permanent deformation of the walls of the tubular portions (6, 7) by a suitable ancillary tool. The clamp provides better stability than known devices, since the two hooks (2, 3) of the clamp cannot move apart owing to their interconnection by deformation of material which clamps them in position relative to each other and avoids the use of components such as nuts and screws. Further, this clamp is small in size and is placed in position by the surgeon in a particularly simply manner.

14 Claims, 8 Drawing Sheets

CLAMP FOR STABILIZING A CERVICAL SPINE SEGMENT

This application is filed under 35 USC 371 based on PCT/EP94/02906 which was filed on Sep. 1, 1994.

BACKGROUND OF THE INVENTION

The present invention relates to a spine osteosynthesis device, in particular a clamp for stabilizing a cervical spine segment, such as the cervical vertebrae C1 and C2.

It is known that certain cervical segments are unstable owing in particular to fractures of cervical vertebrae resulting from accidents on the road or injuries undergone by the intervertebral connections such as the ligaments. Various devices for stabilizing the unstable vertebral segment have therefore been proposed which also permit reducing the time the patient spends in hospital and protecting his nervous system. A known arrangement consists in achieving the stabilization by means of wires binding two cervical vertebrae together. In other known arrangements, the stabilization is achieved by means of two elements hooking onto the vertebrae, interconnected by a screw threaded rod and tightened by nuts, or by means of vertebral screws.

These various techniques present the following drawbacks: first, the stability obtained is insufficient, since the wires are not necessarily tightened in their stable position on the vertebrae. The screw threaded rods interconnecting the hooks to form a clamp stabilizing the vertebral segment may gradually unscrew, since nothing opposes the gradual unscrewing of their tightening nuts. A second drawback resides in the difficulty of placing these devices in position owing to the very deep field of operation due to the flesh covering the vertebrae. A third drawback resides in the inconvenient size of the devices employing screws, hooks and clamps which also present serious neurological risks.

As concerns the wires, their obligatory passage behind the posterior elements of the cervical vertebrae is delicate and involves risks which are well noted in the literature. Further, as the surface of contact between the wires and the bone is small, the "butter cutting wire" phenomenon is frequently observed, and a steel wire has the particularity of easily breaking within a short period, whence a risk of a secondary instability or pseudoarthrosis.

The other implants existing on the market pose the problem of the difficulty of inserting them and often of their overall size and the reliability of the connection between implants.

Besides, the usual connection means between an osteosynthesis rod and spinal anchorage hooks or screws comprise screws, which are not easy to correctly put in place by the surgeon.

SUMMARY OF THE INVENTION

An object of the invention is to provide a clamp for stabilizing a cervical spine segment which reduces or completely eliminates these drawbacks, above all for the cervical segment C1–C2 which is concerned in the most frequent cases of instability pathology.

Another object of the invention is to design a spinal osteosynthesis device whose components, in particular the attachment means between the longitudinal rods and the anchorage members in the vertebrae, are easy to assemble and correctly position.

According to the invention, the clamp comprises a pair of hooks adapted to bear against two cervical vertebrae and each comprising a tubular portion, the diameters of these tubular portions being such as to permit the fitting together and the sliding of one tubular portion in the other and consequently the adjustment of the relative position o the two hooks which may be fixed in this position by a permanent deformation of the walls of the tubular portions.

The clamp arranged in this way provides an improved stability over the aforementioned prior structures, since the two hooks which are part of this clamp cannot move apart owing to the fact that they are interconnected by a permanent deformation of material which clamps them in the chosen relative position. This connection may be achieved by means of a clamp, one of the branches of which is provided with a boss at its end. The clamping of the latter on the two tubular portions fitted one inside the other radially deforms these portions and such a deformation subsequently opposes any sliding or rotation of one of the tubular portions with respect to the other.

The other advantage of this connection by deformation is that it is direct without requirement of an intermediate implant such as screws, rods, nuts, etc., whence an improved reliability and a reduced number of implants and a simplified accessory.

According to a feature of the invention, the tubular portions of the hooks have a circular section. The fact that the section is circular and not for example rectangular enables one of the two hooks to be rotated on the tubular portion of the other, namely the lower hook on the tubular portion of the upper hook after the latter has been placed in position. In tills way, it is possible to suitably orient the lower hook to place t in a position to bear against the lower vertebra before the final interconnection of the two hooks.

According to another feature of the invention, the thicknesses of the two tubular portions are identical Indeed, if these thicknesses were different, the elastic deformation of each of the walls of the tubular portions resulting from the fixing operation would be different and this might result in a clearance owing to the difference in the extent of this deformation between the two walls. Such a clearance would have an adverse effect on the stability of the clamp.

According to another aspect of the invention, the spinal osteosynthesis device comprises a rod which is at least partially tubular and at least one member comprising a tubular body sized to allow a fitting and a sliding on said tubular rod and consequently an adjustment of the relative position of said anchorage member, the latter being fixed in said relative position by a permanent deformation of walls of said tubular rod and tubular body.

According to a further embodiment, the spinal osteosynthesis device includes a second anchorage member and a second rod extending in parallel relationship with said rod; wherein said anchorage members include hooks and one of these hooks is shaped in order that its body be passed through by both second rod and said rod, the two hooks thus forming a clamp.

Further features and advantages of the invention will be apparent from the following description with reference to the accompanying drawings which illustrate miscellaneous embodiments of the invention by way of non-limitative examples.

DESCRIPTION OF THE PREFERRED EMBODIMENTS

Figure 1:
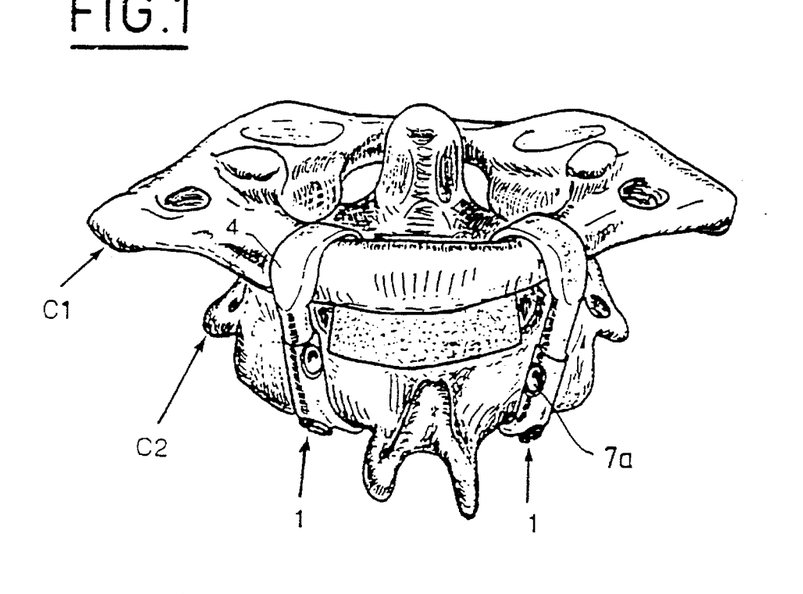
FIG. 1 is a perspective view, to a large scale, of the cervical segment constituted by the first two vertebrae equipped with two stabilizing clamps in accordance with a first embodiment of the invention.

FIG. 1 shows to a large scale the cervical segment formed by the vertebrae C1 and C2, provided with two clamps 1 for stabilizing this segment, placed in position from the rear on each side of the median plane of the segment. Each clamp 1 comprises a pair of hooks 2 and 3 adapted to respectively bear against the laminae of the upper vertebra C1 and lower vertebra C2.

Although these two vertebrae are principally concerned by the clamp according to the invention, it should be noted that the latter is also of use for the stabilization of other cervical vertebrae.

Each hook 2, 3 respectively comprises an end portion 4, 5 constituting the hooking end, and a tubular portion 6, 7 extending from the hooking end. The tubular portion 6 of the upper hook 2 has a length which is much greater than the length of the tubular portion 7 of the lower hook 3 and its dieter is smaller than that of the tubular portion 7 so as to be capable of fitting and sliding in the latter. For this purpose, the tubular portion 7 has both ends open and is therefore slidable with the whole of the hook 3 along the outer surface of the tubular portion 6.

Figure 2:
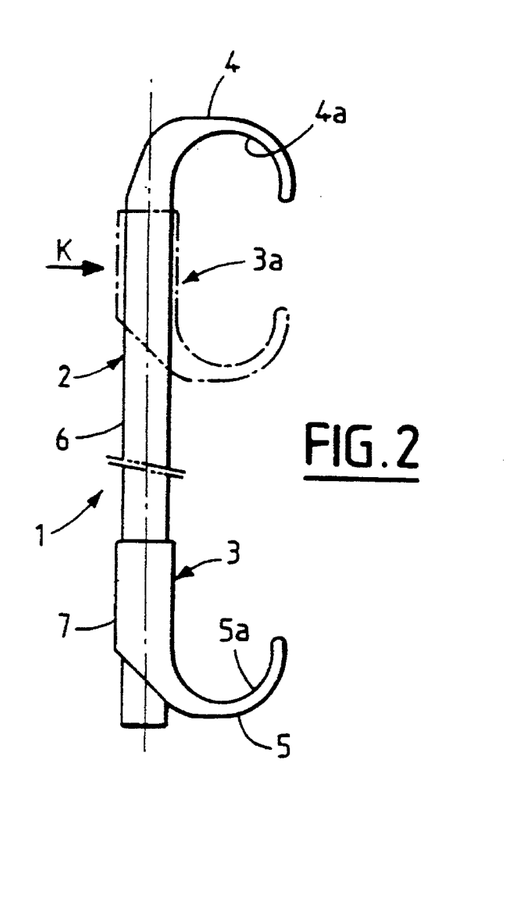
FIG. 2 is an elevational view, to a large scale, with a part cut away, of one of the clamps shown in FIG. 1.
Figure 3:
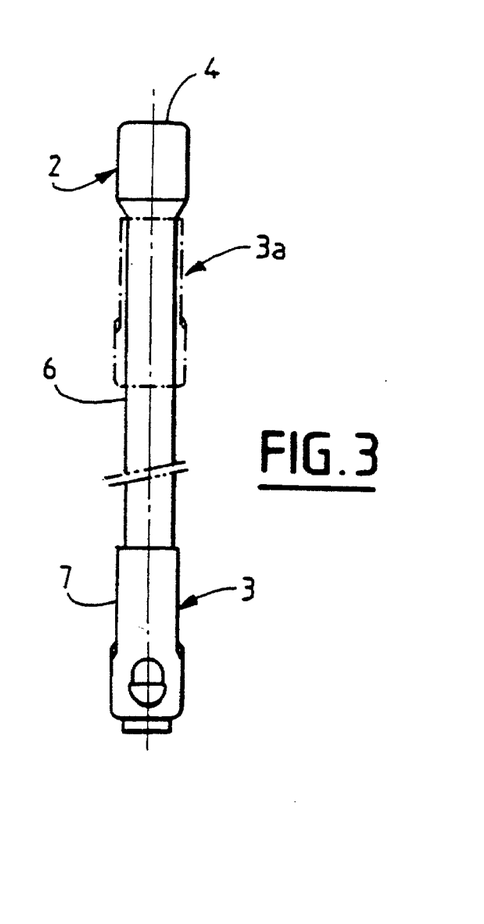
FIG. 3 is an elevational view of the clamp shown in FIG. 2 in the direction of the arrow K.

The tubular portions 6 and 7 have a circular section and the thicknesses of their walls are identical. The terminal hooking portions 4 and 5 have, in the embodiment shown in FIGS. 1 to 3, a wall whose inner surface 4a, 5a has a circular section, the radius of which is of course adapted to the shape of the vertebral laminae onto which they must be hooked.

The operational technique for placing the clamp 1 on vertebrae such as C1 and C2 is the following: the surgeon first of all proceeds to prepare the median fusion site. Thereafter, he inserts the upper hooks, then the lower hooks, puts them under compression by means of a reducing forceps 8 (FIG. 4) known per se, at the same time as the insertion of the spongy tricortical graft, or of a prosthesis for the adepts of the temporary stabilization without arthrodesis, which will be "trapped" in compression between the posterior elements of the two cervical vertebrae. The assembly constructed in this way represents three fixing points which is an assembly reputed to be perfectly stable and reliable.

Figure 4:
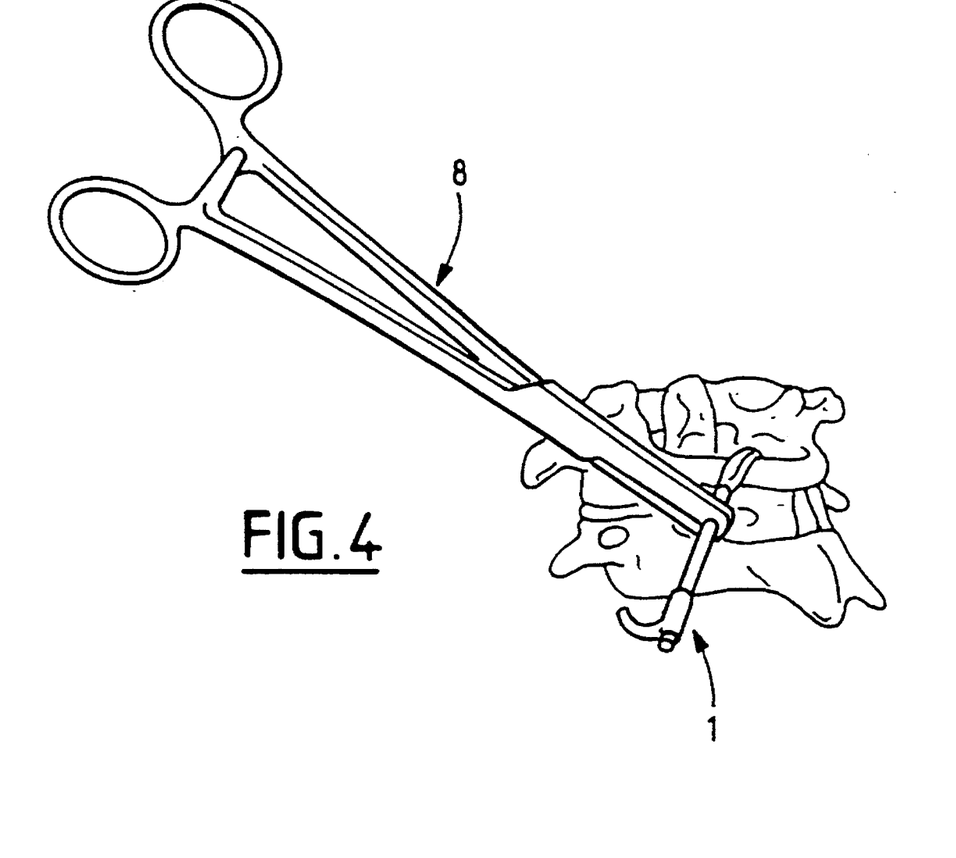
FIG. 4 is a perspective view, to a small scale, of a stage in the operation in which the surgeon places a clamp such as that shown in FIGS. 1 to 3 in position on the vertebral segment C1–C2 by means of a suitable tool.

Then the surgeon places in position first of all the upper hook 2 on the lamina of the upper vertebra C1 by means of the ancillary tool 8 (FIG. 4).

The tubular portion 7 of the hook 3 is mounted on the tubular portion 6 with its curved end portion 5 facing in the posterior direction. The surgeon then pivots the hook 3 on the tubular portion 6 in such manner as to orient it in the plane in which it must be situated for bearing against the corresponding lamina of the vertebra C2. The surgeon then slides by means of an ancillary tool the hook 3 on the tubular portion 6 until the curved end portion 5 comes into contact with the lamina of the vertebra C2. The surgeon then exerts a compression on the forceps to promote the bony fusion and stabilize the assembly. This final position may possibly be the extreme position 3a shown in dot-dash lines in FIG. 2.

Figure 5:
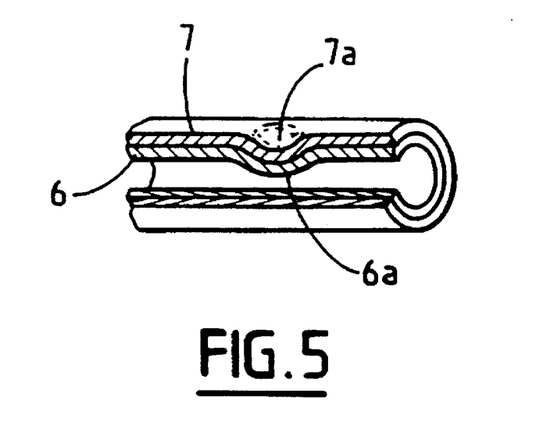
FIG. 5 is a partial perspective view of the region in which two tubular portions of the hooks of the clamp are fixed together after the interconnection of the two hooks by means of a tool (not shown).

Lastly, the surgeon proceeds to the final rigid interconnection of the two hooks 2 and 3 by means of an ancillary tool of known type (not shown), of which the end of one of the branches includes an inner boss. By applying this boss against the tubular portion 7 and clamping together the two branches of the tool, the surgeon exerts on the tubular portion 7, and consequently on the inner tubular portion 6 in this region, sufficient pressure to produce a permanent deformation of the walls of the tubular portions 6 and 7 creating two radial bosses 6a and 7a fitted one inside the other (FIG. 5). It will be understood that after such a deformation, the two tubular portions 6, 7 are finally clamped against a relative translation and rotation, which guarantees a satisfactory stability of the clamp 1 whose two hooks 2, 3 can no longer move apart or rotate one with respect to the other.

Lastly, of course, the surgeon cuts off the part of the tubular portion 6 which projects from the hook 3.

The same sequence of operations is repeated for mounting the second clamp 1.

The clamp according to the invention also has the other following advantages:

Its volume and therefore its overall size are much smaller than those of the aforementioned prior structures.

It can be placed in position by the surgeon in a simple manner as compared with the mounting techniques of the prior devices. Indeed, the design of this clamp permits precise, simple and easy surgical gestures bearing in mind the difficulties resulting from the depth of the operational field. In particular, the structure of the clamp avoids the necessity of the surgeon making gestures in lateral planes for screwing screws or nuts, which is particularly appreciable bearing in mind the depth of the operational field in this region of the spine.

Figure 6:
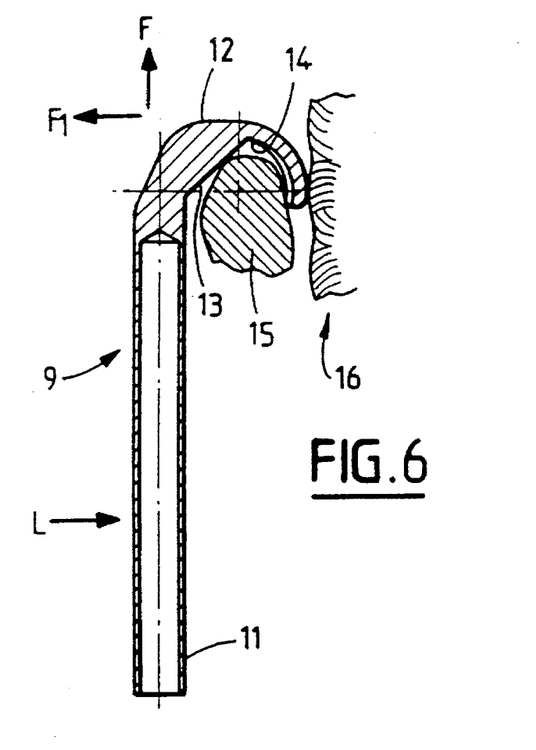
FIG. 6 is a longitudinal sectional view, taken on line 6—6 of FIG. 7, of a second embodiment of the upper hook of the clamp according to the invention.
Figure 8:
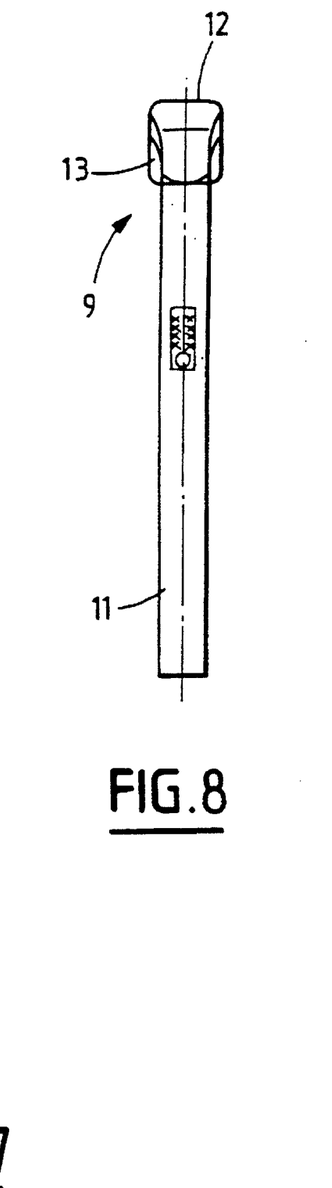
FIG. 8 is an elevational view of the hook in the direction of the arrow L in FIG. 6.

In the second embodiment of the clamp shown in FIGS. 6, 8, the upper hook 9 has, in the extension of its tubular portion 11, a hooking end portion 12 whose inner surface is in two parts: a substantially planar or slightly curved region 13 in the section of which, in planes parallel to the plane of the FIG. 6, the generatrices are rectilinear and which is connected to the tubular portion 11. The region 13 is extended by a terminal region 14 of circular section.

Consequently, whatever be the dimensions or the shape of the lamina 15 of the upper vertebra which is engaged inside the end portion 12 of the hook, this lamina 15 can bear against two different points of the inner surface of the end portion 12, namely a bearing point on the circular surface 14 and a second bearing point on the substantially planar or slightly curved region 13. The bearing of the lamina 15 on the hook 9 is therefore always firm whatever the dimensions of this lamina, and any risk of clearance, which cannot be completely excluded in certain cases with a solely circular bearing section, is then avoided. Further, the clamping of the upper hook 9 and the lower hook to each other produces a clamping force F whose lateral component F1 causes the hook 12 to slide in a direction away from the spinal cord 16. There is therefore an increased safety for the patient, since any risk of damage to the spinal cord is avoided.

Figure 7:
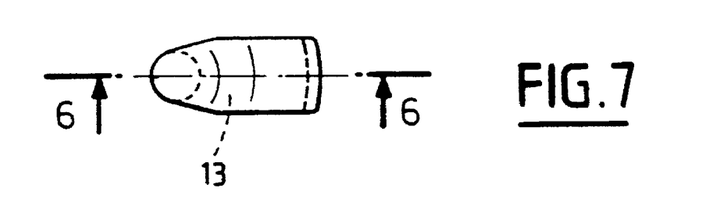
FIG. 7 is a top plan view of the hook shown in FIG. 6.
Figure 9:
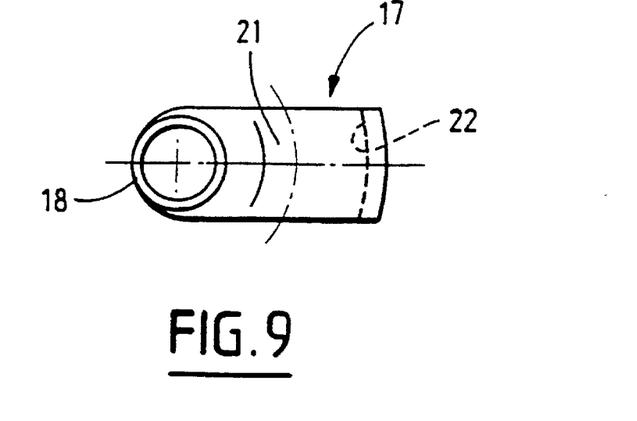
FIG. 9 is a top plan view of a second embodiment of the lower hook of the clamp shown in FIG. 10.
Figure 10:
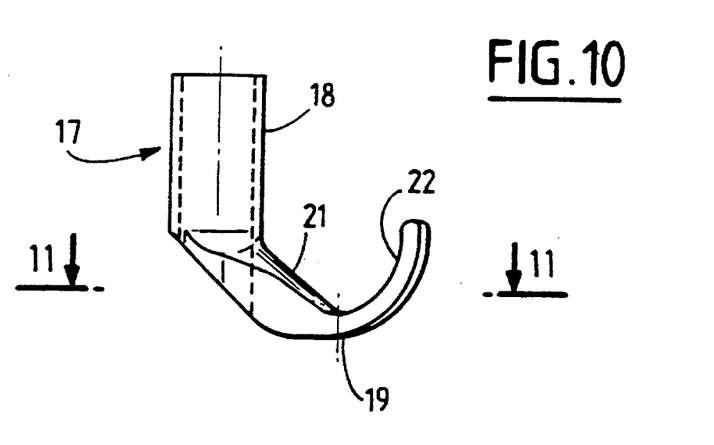
FIG. 10 is a side elevational view of the lower hook shown in FIG. 9.
Figure 11:
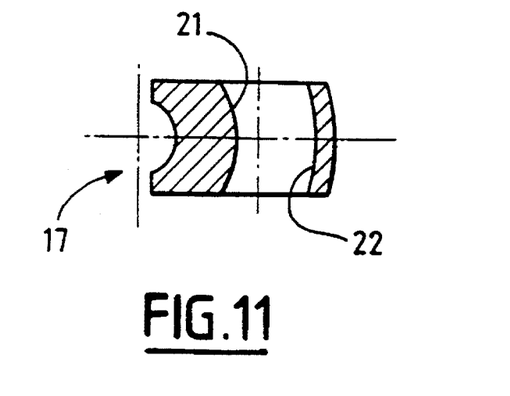
FIG. 11 is a sectional view taken on line 11—11 of FIG. 10.

FIGS. 9 to 11 illustrate a second embodiment of the lower hook 17 whose tubular portion 18 is extended by a curved terminal portion 19 which has two regions: a first region 21 defined in section by a succession of rectilinear generatrices which generate a convex bearing surface (FIG. 11) for the vertebral lamina of the corresponding vertebra, for example C2. The region 21 is connected to the tubular portion 18 and extended by a region 22 of circular section. This particular shape of the hooking end of the lower hook 17 has the same advantages as concerns safety as the arrangement of the upper hook shown in FIGS. 6 to 8. It will be understood that, a clamp formed by two hooks such as those illustrated in FIGS. 6 to 11 have, in addition to this increased safety, all the advantages of the preceding embodiment.

The clamp according to the invention is made from a biocompatible material, advantageously titanium, so as to facilitate the post-operational supervision by all the medical image-foxing means.

Further, among the possible alternative embodiments of the clamp, note that the tubular portions 6 and 7, 11 and 18 may be inverted, the upper hook then having the shortest tubular part.

The indications for the use of the stabilizing clamp according to the invention are the instabilities requiring a posterior approach:

fracture of the odontoid of the vertebra C2, rheumatoid maladies of the spine resulting in instabilities, tumors, congenital malformations, articular luxation fracture, discal luxation and instability of the middle and lower cervical spine.

The invention is also directed to different possible embodiments of a spinal osteosynthesis device shown on FIGS. 12 through 17.

Figure 12:
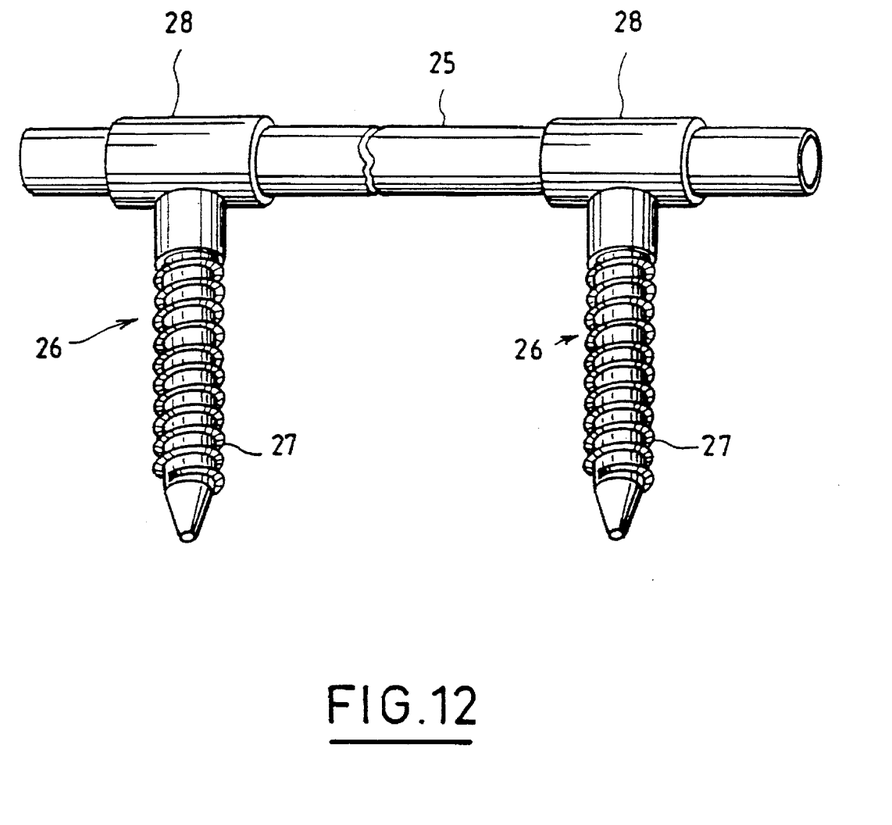
FIG. 12 is a perspective view of a spinal osteosynthesis device according to a third embodiment of the invention.

On FIG. 12, the device comprises one at least partially tubular rod 25 and two spinal anchorage members 26. It should be noted that the device can comprise only one anchorage member 26, the other anchorage members on the rod being different and known per se. In the embodiment shown on FIG. 12, each member 26 is made of a pedicular screw 27 attached to a tubular body 28 the diameter of which is slightly larger than the diameter of the tubular rod 25. This allows a fitting and sliding of bodies 28 on the rod 25 and consequently an adjustment of the relative position of said anchorage members 26.

These members 26 are fixed in the choosen relative position by a permanent deformation of the walls of the rod 25 and tubular bodies 28, in the same manner as shown and disclosed on FIG. 5. The rod 25 can longitudinally extend along a spinal segment to correct spine deviations.

Figure 13:
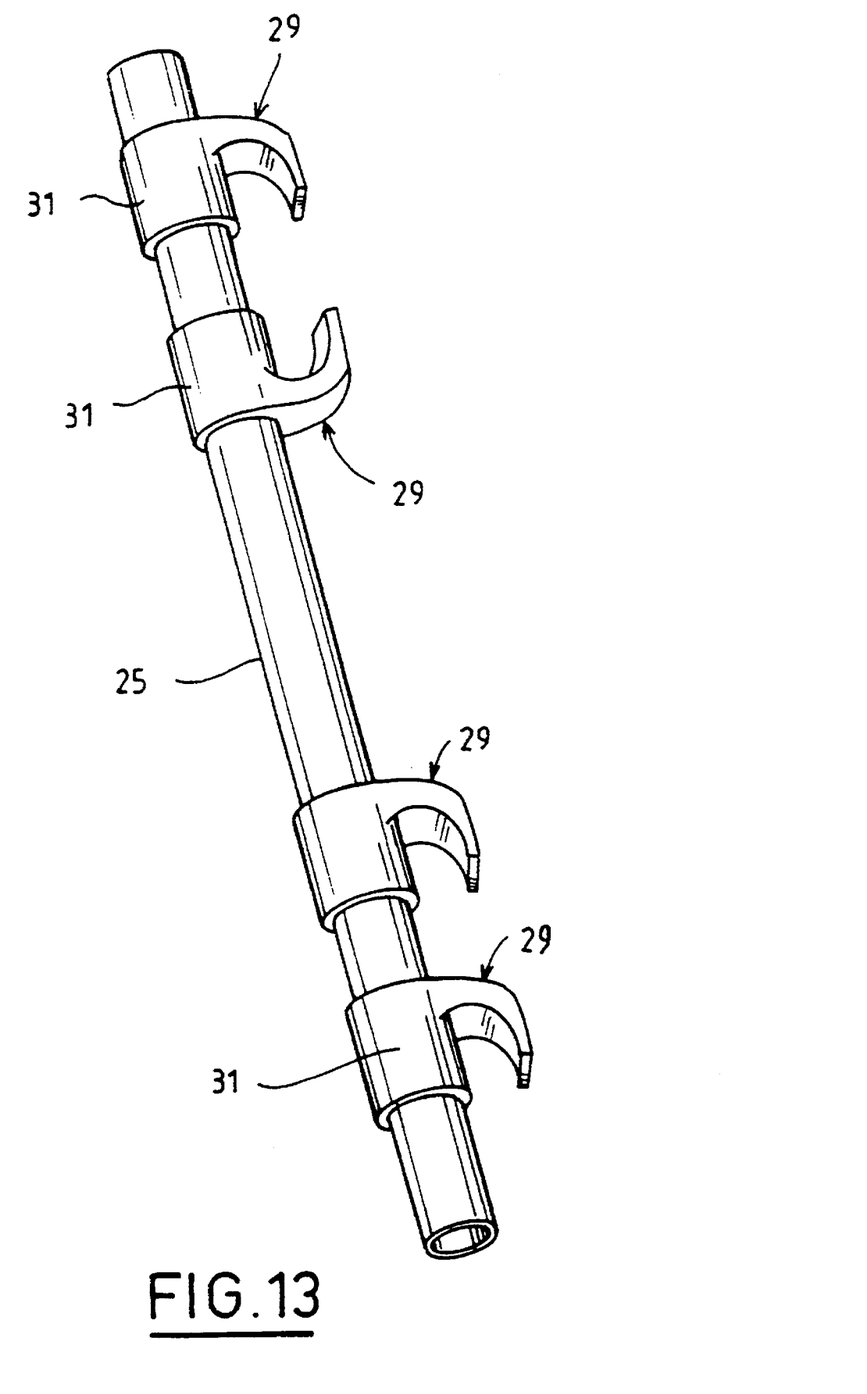
FIG. 13 through 17 are perspective views illustrating five other possible embodiments of the spinal osteosynthesis device according to the invention.

In the embodiments of FIG. 13, the device comprises two pairs of anchorage hooks 29 whose tubular bodies 31 are slidably and adjustably mounted on a longitudinal and rectilinear rod 25. Hooks 29 can be directed in the same or opposite directions according to the needs.

Figure 14:
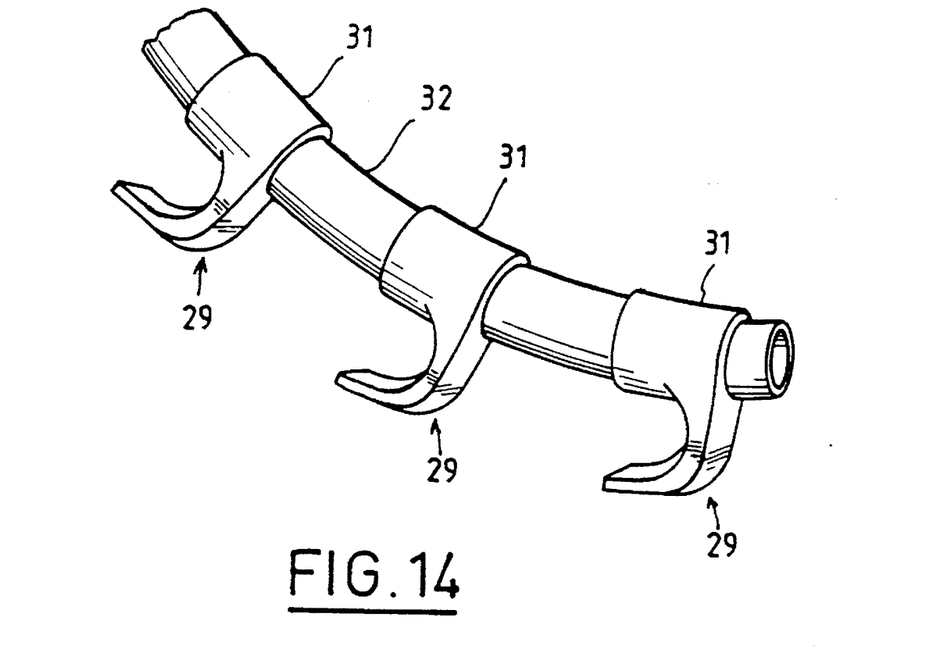

The embodiment of FIG. 14 comprises a bent rod 32 slidingly bearing three anchorage hooks 29.

Figure 15:
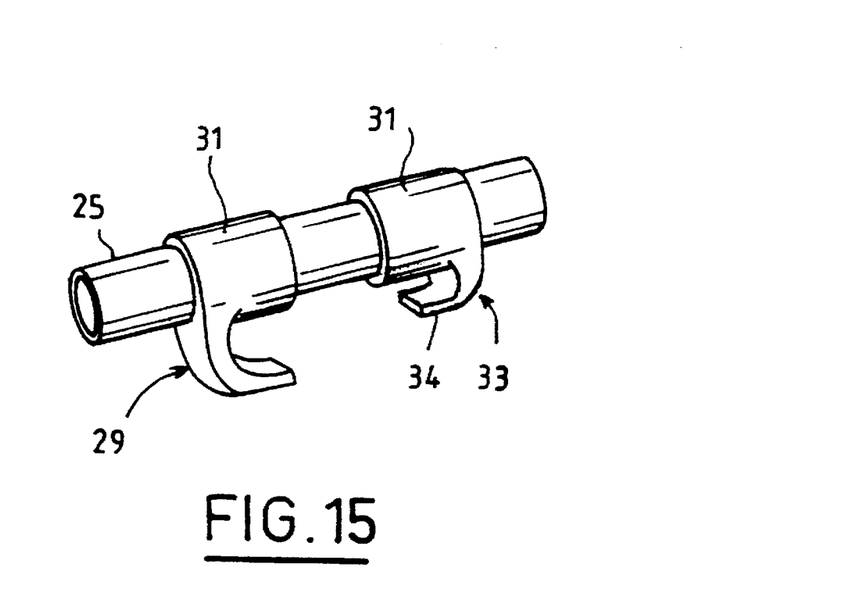

In the embodiment of FIG. 15, which is provided with two anchorage hooks 29, 33, hook 33 has a blade 34 smaller than the blade of the other hook 29 and which is oriented in the opposite direction. Thus both hooks 29 and 33 form an adjustable clamp, hook 33 being a stabilization member.

Figure 16:
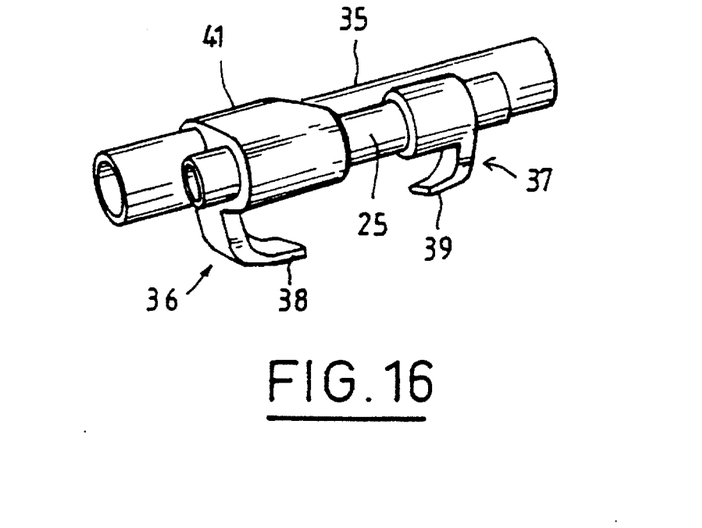

The device shown on FIG. 16 comprises, besides tubular rod 25, a second rod 35 extending longitudinally along the spine (not illustrated) and in parallel relationship with tubular rod 25. The anchorage members are two hooks 36 and 37 whose blades 38, 39 are directed one towards the other so as to form a clamp.

The hook 36 is shaped in order that its body 41 comprises two parallel bores passed through respectively by rods 35 and 25, rod 35 having a diameter larger than rod 25 and being intended to longitudinal extend along a spine segment.

Due to the difference of diameters between rods 35 and 25, the hook 37 is smaller than hook 36. The rod 35 can be full or tubular.

Figure 17:
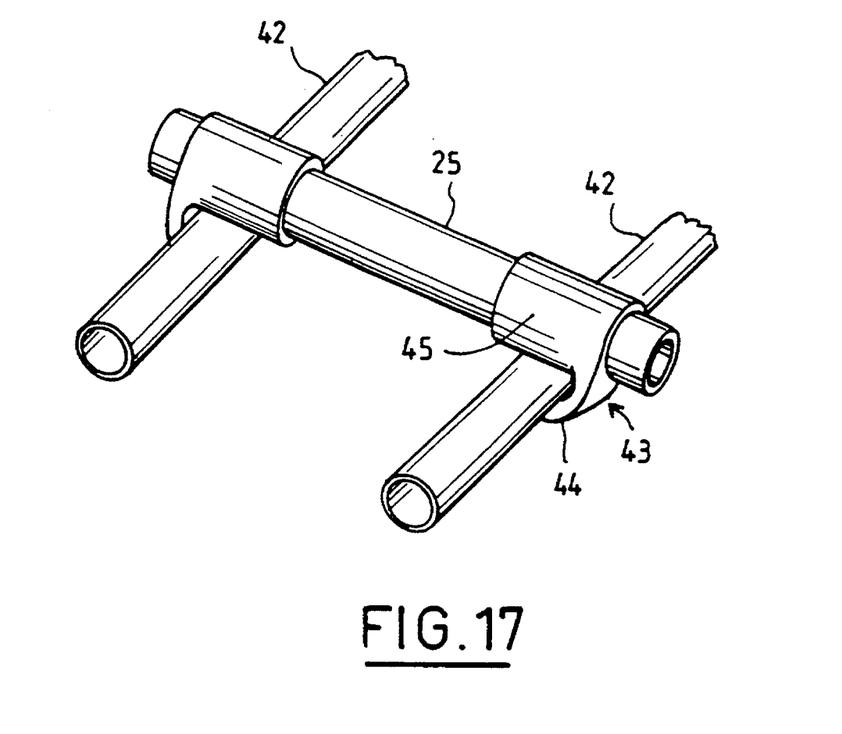

In the embodiment illustrated on FIG. 17, the device contemplated by the invention forms a transverse connection means between two longitudinal osteosynthesis tubular rods 42 extending along a spine segment.

The connection device comprises a tube 25, the diameter of which can be equal or different from the diameters of rods 42, and two fixation hooks 43. The latter each comprise a blade 44 adapted to fit on the associated rod 42, and a tubular body 45 which can slide over the rod 25 and be fixed on the same in the above described manner.

Anchorage screws other than pedicular screws can be used, and miscellaneous devices incorporating a number of combinations of the above disclosed means, with rectilinear or curved rods, and full or tubular rods, can be designed according to the invention.

The advantages of these devices in respect to the prior art (full and rigid longitudinal rods which they can replace) are the following: the assembly by permanent deformation of the tubes by crimping is easy to perform, the positioning of the elements is simplified and requires a low number of mounting tools.

What is claimed is:

1. Clamp for stabilizing a cervical spine segment comprising; a pair of hooks for bearing against two cervical vertebrae, each hook including a tubular portion, one of the tubular portions having a diameter smaller than the diameter of the other of the tubular portions as to permit a sliding fit of said one tubular portion in said other of the tubular portions and consequently an adjustment of the relative position of said two hooks, said tubular portions being mechanically crimped together so as to fix said hooks in said relative position.

2. Clamp according to claim 1, wherein said tubular portions have a circular section.

3. Clamp according to claim 1, wherein said one of the tubular portions is longer than said other of the tubular portions.

4. Clamp according to claim 3, wherein said one of the tubular portions has both ends open so as to permit the fitting of said other of the tubular portions inside said one of the tubular portions.

5. Clamp according to claim 1, wherein said two tubular portions comprise walls having identical thicknesses.

6. Clamp according to claim 5, wherein said one of the tubular portions has both ends open so as to permit the fitting of said other of the tubular portions inside said one of the tubular portions.

7. Clamp according to claim 1, wherein each of said hooks has a hooking end portion of circular section.

8. Clamp according to claim 1, wherein each of said hooks has a hooking end portion defining an inner surface which includes, in the extension of said tubular portion, a substantially planar region having rectilinear generatrices in a section in the plane of said hooking end portion.

9. Clamp according to claim 1, wherein each of said hooks has a hooking end portion defining an inner surface which includes, in the extension of said tubular portion, a substantially curved region having rectilinear generatrices in a section in the plane of said hooking end portion.

10. Spine osteosynthesis device, comprising: a first tubular spinal rod configured to extend longitudinally along a spine segment; and at least one first anchorage member comprising a first tubular body portion and an anchorage portion; said first tubular body portion sized to allow a sliding fit with said first spinal rod and consequently an adjustment of the relative position of said first anchorage member and said first spinal rod, said first spinal rod and said first tubular body portion being mechanically crimped together so as to fix said first body portion in said relative position along said first spinal rod.

11. Spine osteosynthesis device according to claim 10, wherein said anchorage portion comprises a bone screw.

12. Spine osteosynthesis device according to claim 10, wherein said anchorage portion comprises a spinal hook.

13. Spinal osteosynthesis device according to claim 12, further comprising: a second tubular spinal rod and a second anchorage member; said second anchorage member comprising a second tubular body portion and a spinal hook; said second tubular body portion having two openings therethrough to receive said first and second spinal rods in a substantially parallel manner, said first anchorage member being positioned on said first spinal rod in an opposing manner to said second anchorage member so as to form a clamping arrangement between the respective spinal hooks of said first and second anchorage members.

14. Spinal osteosynthesis device according to claim 10, forming a transverse connection means between two spinal rods extending longitudinally along a spine segment, and including at least two of said anchorage members, said anchorage portions of the respective anchorage members being configured to form hooks adapted to clamp a respective spinal rod.

* * * * *